United States Patent
Caballero Tapia et al.

(10) Patent No.: US 12,397,077 B2
(45) Date of Patent: Aug. 26, 2025

(54) DEVICE FOR DIFFUSING VOLATILE SUBSTANCES

(71) Applicant: ZOBELE HOLDING SPA, Trento (IT)

(72) Inventors: Moises Caballero Tapia, Barcelona (ES); Alba Graus Ferrer, Barcelona (ES); Roberto Camarero Diez, Barcelona (ES)

(*) Notice: Subject to any disclaimer, the term of this patent is extended or adjusted under 35 U.S.C. 154(b) by 34 days.

(21) Appl. No.: 17/416,321

(22) PCT Filed: Dec. 19, 2019

(86) PCT No.: PCT/EP2019/086393
§ 371 (c)(1),
(2) Date: Jun. 18, 2021

(87) PCT Pub. No.: WO2020/127793
PCT Pub. Date: Jun. 25, 2020

(65) Prior Publication Data
US 2022/0072179 A1    Mar. 10, 2022

(30) Foreign Application Priority Data
Dec. 21, 2018    (ES) .................................. 201831262

(51) Int. Cl.
*A01M 1/20*    (2006.01)
*A61L 9/03*    (2006.01)

(52) U.S. Cl.
CPC .............. *A61L 9/03* (2013.01); *A01M 1/2066* (2013.01)

(58) Field of Classification Search
CPC .......... A61L 9/03; A61L 9/037; A01M 1/2066
See application file for complete search history.

(56) References Cited

U.S. PATENT DOCUMENTS

| | | | |
|---|---|---|---|
| 5,150,541 A | * | 9/1992 | Foster .................. A01M 1/2005 43/131 |
| 6,286,248 B1 | | 9/2001 | Bryant |
| 2010/0215549 A1 | | 8/2010 | Corda |

FOREIGN PATENT DOCUMENTS

| | | |
|---|---|---|
| FR | 2215864 A5 | 8/1974 |
| WO | 2020127793 A1 | 6/2020 |

OTHER PUBLICATIONS

Gong, R.H., "Specialist Yarn and Fabric Structures: Developments and Applications." 2011. Woodhead Publishing. Chapter 14. pp. 333-353. (Year: 2011).*
International Search Report and Written Opinion for PCT/EP2019/086393; Mailed Mar. 26, 2020.

* cited by examiner

*Primary Examiner* — Timothy C Cleveland
(74) *Attorney, Agent, or Firm* — Kutak Rock LLP

(57) ABSTRACT

The device for diffusing volatile substances comprises a body (1) impregnated with volatile substances, with the volatile substances diffusing during the combustion of the body (1), wherein the body (1) comprises a plurality of interwoven threads (2). Furthermore, the interwoven threads (2) may be housed inside a tube (3). Thanks to this interwoven arrangement of the threads that make up the body, the oxygen between the threads facilitates combustion, without needing to use chemical components that stimulate combustion.

11 Claims, 1 Drawing Sheet

DEVICE FOR DIFFUSING VOLATILE SUBSTANCES

This is the United States National Stage of Patent Cooperation Treaty Application No. PCT/EP2019/086393 filed Dec. 19, 2019, which claims priority to Spanish Patent Application No. P20181262, filed on Dec. 21, 2018, the disclosures of which are incorporated herein by reference in their entireties.

The present invention relates to a device for diffusing volatile substances, specifically, for diffusing a volatile active insecticide.

BACKGROUND OF THE INVENTION

Different types of devices for diffusing volatile substances such as insecticides or air-fresheners are known.

One type of these diffusion devices uses the slow combustion of a material for the slow or controlled release of said volatile substances.

There are two main groups of devices identified with these features: what are referred to as insecticide coils and combustion paper. The coils require a slow-burning agent to ensure uniform combustion, and the combustion paper poses a safety hazard.

Other drawbacks of the existing solutions are that the coils provide a slow and controlled release of active ingredients, but they require chemical ingredients to ensure proper combustion.

Furthermore, the coils are not easily customisable according to the existing manufacturing processes.

Moreover, combustion paper solutions intrinsically pose a high risk of fire, and they also have a fast burning time, which can lead to a short usage time.

Therefore, one objective of the present invention is to provide a device for diffusing volatile substances which enables suitable combustion of the active ingredients at a suitable speed, without needing to use chemical ingredients as a combustion agent.

DESCRIPTION OF THE INVENTION

The diffusion device of the invention resolves the aforementioned drawbacks, presenting other advantages that are described below.

The device for diffusing volatile substances according to the present invention comprises a body impregnated with said volatile substances, with the volatile substances diffusing during the combustion of said body, wherein said body comprises a plurality of interwoven threads.

Thanks to this interwoven arrangement of the threads that make up the body, the oxygen between the threads facilitates combustion, without needing to use chemical components that stimulate combustion.

Advantageously, said interwoven threads are housed inside a tube, for example, a woven tube, and, if desired, said body may comprise a plurality of tubes made of interwoven threads.

According to this embodiment, said tubes made of interwoven threads are preferably housed inside a sheath, and said tubes can be interwoven.

Preferably, said threads have a diameter of between 0.2 mm and 2 mm and the number of interwoven threads is between 2 and 30 threads. Furthermore, the number of tubes made of interwoven threads is preferably between 2 and 10.

Advantageously, the threads, the tube or tubes and the sheath are made of a natural material, such as cotton or linen or any suitable natural material, without using any chemical product to assist combustion.

If desired, the body may also be impregnated with one or more essential or natural oils, such as, citronella, geranium, neem, citrus, tomato leaves, rosemary, eucalyptus, lemongrass, cedar wood and/or lavender. Said essential or natural oils are preferably dissolved in a solvent, such as non-polar solvents, acetone, isoparaffin, glycol ethers or other naturally derived solvents.

Furthermore, for use, said body is elongated and hung from a support by the upper end thereof, such that the combustion starts from the lower end.

BRIEF DESCRIPTION OF THE DRAWINGS

To provide a better understanding of the description, a series of drawings are included that schematically, and by way of illustration and not limitation, represent a practical embodiment of the invention.

DESCRIPTION OF A PREFERRED EMBODIMENT

Figure 1:
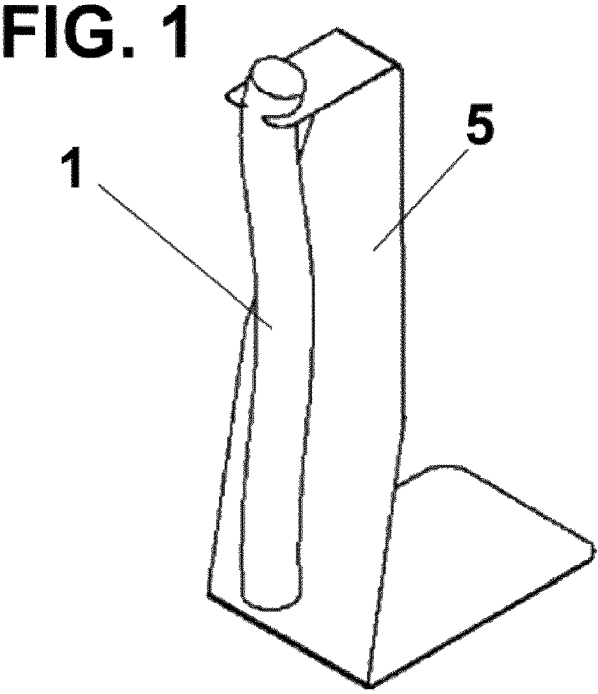
FIG. 1 is a perspective view of the device for diffusing volatile substances according to the present invention, formed by a body hanging from a support.

As shown in FIG. 1, the device for diffusing volatile substances comprises a body (1) impregnated with volatile substances, which could be, for example, insecticides or air-freshener substances, and a support (5) from which the body (1) hangs from the upper end thereof.

Figure 2:
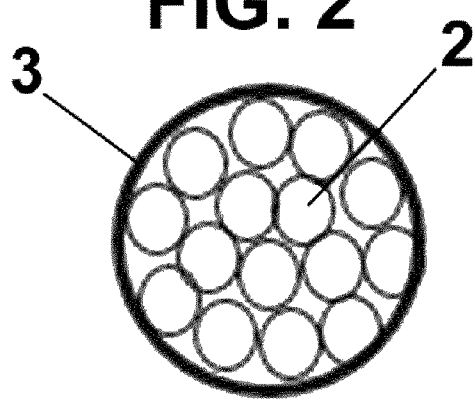
FIG. 2 is a cross-sectional view of a body formed by a tube of the body, comprising a plurality of interwoven threads.

Said body comprises a plurality of interwoven threads (2), forming a braided cord, with said threads (2) made of a natural material, for example, cotton. These interwoven threads (2), can be covered with a tube (3) (FIG. 2) made of the same natural material or of another suitable material, preferably natural. Said tube (3) may be made up of woven threads.

Only by way of example, the interwoven threads (2) number between 2 and 30, and the diameter of each thread 2 may vary between 0.2 mm and 2 mm, with all of the threads (2) able to have the same diameter or different diameters.

The interwoven threads (2), due to the oxygen present between them, enable continuous combustion, without needing for an additional combustion agent, such as potassium nitrate, for example.

The natural construction of the tube (3) also enables oxygen to flow through the gaps between the threads thereof, which enables slow combustion to be produced without extinguishing and without needing for additional combustion agents.

The threads (2) can be manufactured with natural materials such as cotton (recycled and/or virgin), linen, etc. Furthermore, the woven tube 3, if it is included, can be manufactured with the same material as the threads (2), or with a different material. The woven tube 3 can also be made with different thread colors in order to personalise and differentiate it.

The body (1) is impregnated with a solution which includes a volatile active ingredient for insecticide or air-freshener purposes.

For example, such active ingredients could include pyrethroids and essential oils with insecticide or repellent properties and other ingredients such as solvents. These solvents may be non-polar, acetone, isoparaffin, glycol ethers and other naturally derived solvents.

As indicated above, the body 1 hangs from the support 5, which preferably has the shape of a stamped piece of metal, which holds it from the top end.

A user will ignite the lower end with a flame. When the lower end has been ignited, the user will blow out the flame, initiating the slow-combustion reaction, which will burn the entire length of the body 1.

During this combustion process, due to the high temperature generated, the volatile substances will change to a gaseous state, be released into the surrounding air and provide protection against mosquitoes and/or other insects or they will perfume the environment.

Figure 3:
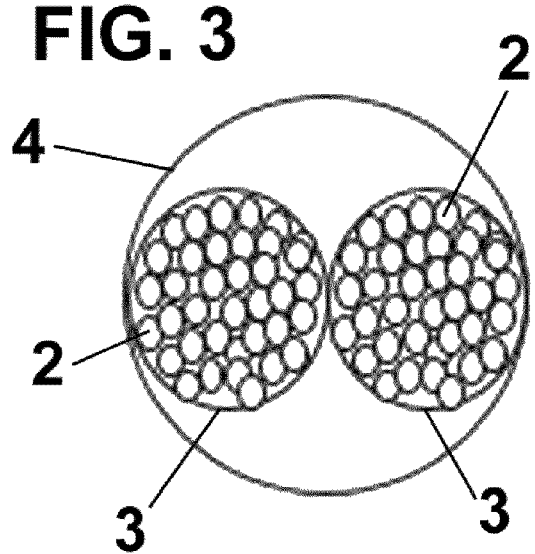
FIG. 3 is a cross-sectional view of a body formed by a sheath which houses two tubes made of interwoven threads therein.

FIG. 3 shows another possible embodiment of the body (1). In this embodiment, a plurality of tubes 3 with the interwoven threads (2) therein, for example, from 2 to 10 tubes, are housed in a sheath (4), which is also preferably made of natural material, for example, cotton or linen. The tubes 3, also interwoven, are preferably arranged inside the sheath (4), although they could be arranged in any other suitable manner.

Although reference has been made to a specific embodiment of the invention, it is clear for a person skilled in the art that numerous variations and modifications may be made to the diffusion device described, and that all of the details mentioned may be substituted with other technically equivalent details, without falling outside the scope of protection defined by the attached claims.

The invention claimed is:

1. A device for diffusing volatile substances, comprising a vertical support structure (5) and a body (1) impregnated with said volatile substances, with the volatile substances diffusing during the combustion of said body (1), characterised in that said body (1) comprises a plurality of interwoven threads (2);

wherein said interwoven threads (2) are housed inside a tube (3);

wherein said body (1) is substantially elongated and comprises a plurality of tubes (3), each tube (3) covering interwoven threads (2);

wherein said tubes (3) of interwoven threads (2) are housed inside a sheath (4);

wherein said vertical support structure (5) is substantially elongated and comprises a lower end and an upper end, said lower end including a base, and said upper end configured to receive the top end of said body (1);

wherein the top end of said body (1) hangs from the upper end of the support structure (5) such that the upper end of the support structure (5) contacts the top end of said body (1); and wherein the body (1) is configured such that combustion begins at the bottom end.

2. The device for diffusing volatile substances according to claim 1, wherein said tubes (3) are interwoven.

3. The device for diffusing volatile substances according to claim 1, wherein said threads (2) have a diameter between 0.2 mm and 2 mm.

4. The device for diffusing volatile substances according to claim 1, wherein the number of interwoven threads (2) is between 2 and 30 threads.

5. The device for diffusing volatile substances according to claim 1, wherein the number of tubes (3) made of interwoven threads (2) is between 2 and 10.

6. The device for diffusing volatile substances according to claim 1, wherein the threads (2) are made of a natural material.

7. The device for diffusing volatile substances according to claim 1, wherein the tube(s) (3) and/or sheath (4) are made of a natural material.

8. The device for diffusing volatile substances according to claim 1, wherein said body (1) is also impregnated with one or more essential or natural oils.

9. The device for diffusing volatile substances according to claim 8, wherein said essential or natural oils are dissolved in a solvent.

10. The device for diffusing volatile substances according to claim 1, wherein said body (1) is elongated.

11. The device for diffusing volatile substances according to claim 1, wherein the number of interwoven threads (2) is between 4 and 30 threads.

* * * * *